US00PP24543P2

(12) United States Plant Patent
Ramirez

(10) Patent No.: US PP24,543 P2
(45) Date of Patent: Jun. 10, 2014

(54) ***SOLENOSTEMON* PLANT NAMED 'BALCONISP'**

(50) Latin Name: *Solenostemon scutellarioides*
Varietal Denomination: Balconisp

(75) Inventor: Rolando Solano Ramirez, Dulce Nombre de Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 162 days.

(21) Appl. No.: 13/507,910

(22) Filed: Aug. 6, 2012

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

PUBLICATIONS

Upov pluto citations for 'balconisp' Jan. 2012.*

* cited by examiner

*Primary Examiner* — Wendy C Haas
(74) *Attorney, Agent, or Firm* — Audrey Charles

(57) ABSTRACT

A new and distinct cultivar of *Solenostemon* plant named 'Balconisp', characterized by its mixed creamy yellow-orange, green, and burgundy colored foliage, and vigorous, upright growth habit, is disclosed.

1 Drawing Sheet

Latin name of genus and species of plant claimed: *Solenostemon scutellarioides.*

Variety denomination: 'Balconisp'.

BACKGROUND OF THE INVENTION

The present invention relates to a new and distinct cultivar of *Solenostemon* plant botanically known as *Solenostemon scutellarioides* and hereinafter referred to by the cultivar name 'Balconisp'.

The new cultivar originated in a controlled breeding program in Cartago, Costa Rica during January 2008. The objective of the breeding program was the development of *Solenostemon* cultivars with unique foliage coloration and leaf shape, upright growth habit, and good sun tolerance.

The new *Solenostemon* cultivar is the result of cross-pollination. The female (seed) parent of the new cultivar is 'Florida City Raiford', not patented, characterized by deep burgundy, yellow, and green colored foliage and vigorous, upright growth habit. The male (pollen) parent of the new cultivar is the proprietary *Solenostemon scutellarioides* breeding selection coded Co7034, not patented, characterized by its medium golden-colored foliage with green-colored margins and vigorous, upright growth habit. The new cultivar was discovered and selected as a single flowering plant within the progeny of the above stated cross-pollination during July 2008 in a controlled environment in Cartago, Costa Rica.

Asexual reproduction of the new cultivar by terminal stem cuttings since July 2008 in Cartago, Costa Rica and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balconisp' as a new and distinct cultivar of *Solenostemon* plant:

1. Mixed creamy yellow-orange, green, and burgundy colored foliage, and
2. Vigorous, upright growth habit.

Plants of the new cultivar differ from plants of the female parent primarily in foliage color shades and distribution pattern and from plants of the male parent primarily in foliage color.

Of the many commercially available *Solenostemon* cultivars, the most similar in comparison to the new cultivar is COLORBLAZE 'Royal Glissade', not patented. However, in side by side comparisons, plants of the new cultivar differ from plants of 'Royal Glissade' in at least the following characteristics:

1. Plants of the new cultivar are taller than plants of 'Royal Glissade';
2. Plants of the new cultivar are narrower than plants of 'Royal Glissade'; and
3. Plants of the new cultivar have a stem color different from plants of 'Royal Glissade'.

BRIEF DESCRIPTION OF THE PHOTOGRAPHS

The accompanying photographs show, as nearly true as it is reasonably possible to make the same in color illustrations of this type, and typical foliage characteristics of the new cultivar. Colors in the photographs differ slightly from the color values cited in the detailed description, which accurately describes the colors of 'Balconisp'. The plants were grown in 4-inch pots for 8 weeks in a greenhouse in West Chicago, Ill.

DETAILED BOTANICAL DESCRIPTION

Figure 1:
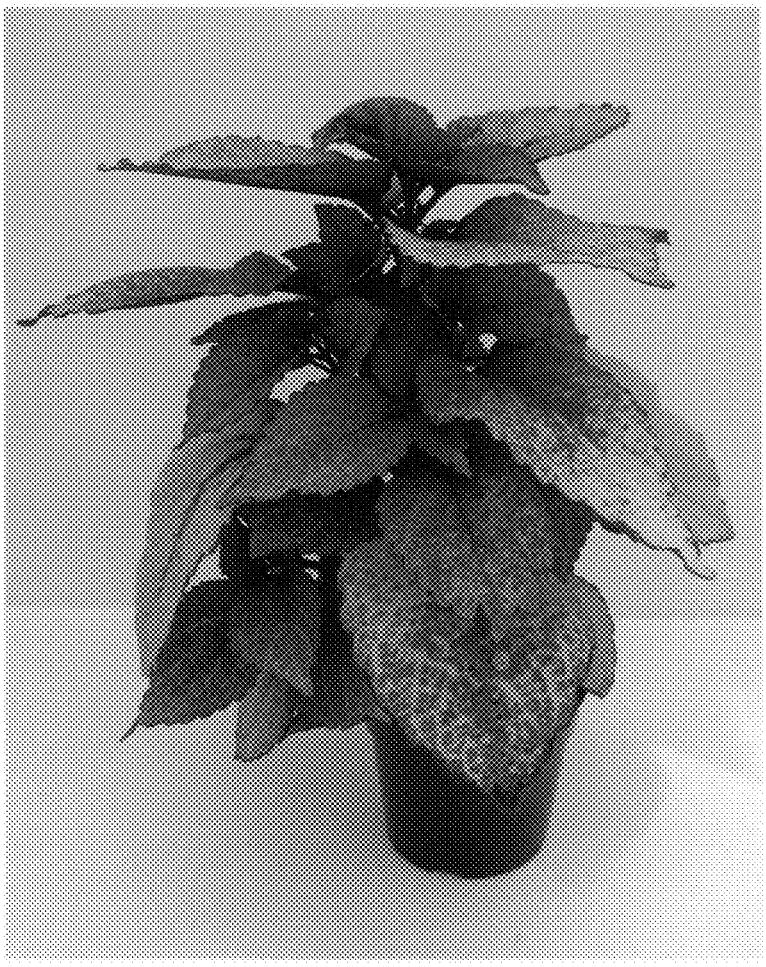
FIG. 1 illustrates a side view of the overall growth habit of 'Balconisp'.
Figure 2:
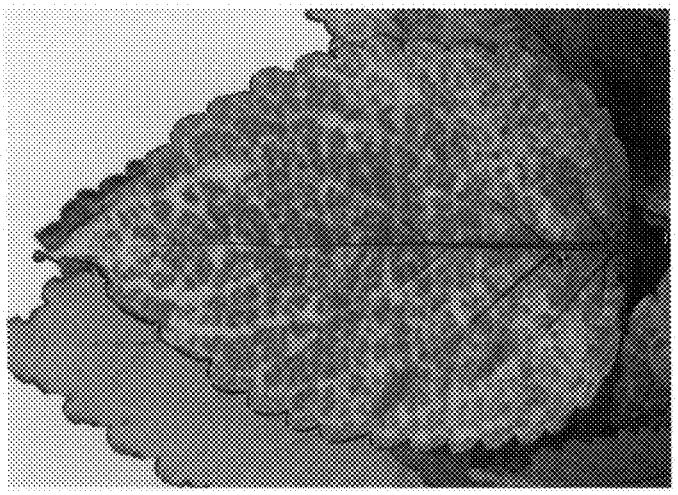
FIG. 2 illustrates a close-up view of an individual leaf of 'Balconisp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2012 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Solenostemon scutellarioides* cultivar Balconisp.

Parentage:

*Female parent*.—'Florida City Raiford', not patented.

*Male parent*.—Proprietary *Solenostemon scutellarioides* breeding selection coded Co7034, not patented.

Propagation:

*Type cutting*.—Terminal stem.

*Time to initiate roots*.—Approximately 4 to 6 days.

*Time to produce a rooted cutting*.—Approximately 21 to 24 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Vigorous, upright.

*Size*.—Height from soil level to top of plant plane: Approximately 28.2 cm. Width: Approximately 24.6 cm.

*Branching habit*.—Freely branching, pinching improves basal branching. Quantity of lateral branches per plant: Approximately 8.

*Branch*.—Strength: Strong. Shape: Square in cross section. Length of lateral branch: Approximately 9.8 cm. Diameter of lateral branch at central internode: Approximately 4.0 mm. Length of central internode of lateral branch: Approximately 1.5 cm. Texture: Densely pubescent with short hairs. Color of young and mature stems: 187A with mottling of 143B.

Foliage description:

*General description*.—Quantity of leaves per main stem: Approximately 6. Fragrance: None. Form: Simple. Arrangement: Opposite.

*Leaves*.—Aspect: Petiole is at an acute angle to stem; leaf blade is perpendicular to stem and transitions to an obtuse angle with age. Appearance: Dull. Shape: Ovate. Margin: Crenate. Apex: Acute. Base: Attenuate. Venation pattern: Pinnate. Length of mature leaf: Approximately 10.8 cm. Width of mature leaf: Approximately 8.5 cm. Texture of upper surface: Sparsely pubescent. Texture of lower surface: Sparsely pubescent with dense pubescence on venation. Color of upper surface of young and mature foliage: Irregular distribution of 137A, 143A, 19D, and 187B; midveins and margins of 187A; other venation indistinguishable from lamina. Color of lower surface of young and mature foliage: 185B to 185C with venation of 187A.

*Petiole*.—Length: Approximately 3.8 cm. Width: Approximately 3.0 mm. Texture: Densely pubescent with short hairs. Pubescence color: A mixture of colorless, transparent and 187A. Color: 187A.

Flowering description: Flowers are ornamentally insignificant for this variety. No flowers were observed in this trial.

Seed and fruit production: Neither seed nor fruit production has been observed.

Disease and pest resistance: Resistance to pathogens and pests common to *Solenostemon* has not been observed.

What is claimed is:

1. A new and distinct cultivar of *Solenostemon* plant named 'Balconisp', substantially as herein shown and described.

* * * * *